United States Patent
Asthana et al.

(10) Patent No.: US 11,927,537 B2
(45) Date of Patent: Mar. 12, 2024

(54) RAPID, LOW-COST PROCESS FOR THE PREPARATION OF SERS SUBSTRATE AND SERS SUBSTRATE PREPARED THEREBY

(71) Applicant: COUNCIL OF SCIENTIFIC AND INDUSTRIAL RESEARCH, New Delhi (IN)

(72) Inventors: Amit Asthana, Hyderabad (IN); Mohan Rao Chintalagiri, Hyderabad (IN); Saurabh Kumar Srivastava, Hyderabad (IN); Gopi Suresh Oggu, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 572 days.

(21) Appl. No.: 17/256,555

(22) PCT Filed: Feb. 8, 2019

(86) PCT No.: PCT/IN2019/050102
§ 371 (c)(1),
(2) Date: Dec. 28, 2020

(87) PCT Pub. No.: WO2020/003321
PCT Pub. Date: Jan. 2, 2020

(65) Prior Publication Data
US 2021/0156804 A1  May 27, 2021

(30) Foreign Application Priority Data
Jun. 27, 2018 (IN) .............................. 201811023895

(51) Int. Cl.
*G01N 21/65* (2006.01)
*G01N 33/543* (2006.01)
*B82Y 15/00* (2011.01)

(52) U.S. Cl.
CPC ..... *G01N 21/658* (2013.01); *G01N 33/54346* (2013.01); *B82Y 15/00* (2013.01)

(58) Field of Classification Search
CPC ........... G01N 21/658; G01N 33/54346; B82Y 15/00; B82Y 30/00
See application file for complete search history.

(56) References Cited

U.S. PATENT DOCUMENTS 9,329,177 B2   5/2016  Chattopadhyay et al.

FOREIGN PATENT DOCUMENTS

WO   2010/073260 A1   7/2010

OTHER PUBLICATIONS

Whatman qualitative filter paper, Grade 1, printed Sep. 5, 2023.*
(Continued)

*Primary Examiner* — Rebecca C Bryant
(74) *Attorney, Agent, or Firm* — Blank Rome LLP (57) ABSTRACT

The present invention relates to a cost effective and single step process for rapid manufacturing of paper-based SERS substrates (100), wherein chitosan is used for direct in situ reduction of the metallic precursor solutions for production of metallic nanoparticles on the substrates. The crucial step in the process involves the incubation of the paper-based substrates under humidifying conditions at an elevated temperature for a predetermined duration. The metal nanoparticles thus produced are homogenously deposited over the paper-based substrate making the paper-based substrate suitable for SERS analysis. The paper-based substrate thus developed is cost-effective, flexible, easy to load and is demonstrated to have exceptional sensitivity with detection limits of up to 1 pM.

17 Claims, 6 Drawing Sheets

(56) References Cited

OTHER PUBLICATIONS

Smolsky J, Kaur S, Hayashi C, Batra SK, Krasnoslobodtsev AV. Surface-Enhanced Raman Scattering-Based Immunoassay Technologies for Detection of Disease Biomarkers. Frosch T, ed. Biosensors. 2017;7 (I):7.
Fleischmann, M., Hendra, P. J. and McQuillan, A. J., Raman spectra of pyridine adsorbed at a silver electrode. Chem. Phys. Lett., 1974, 26, 163-166.
Sharma, B., Frontiera, R.R., Henry, A.I., Ringe, E., Van Duyne, R.P., SERS: materials, applications, and the future, Mater today 15(1), 2012, 16-25.
Dalla Marta, S., Novara, C., Giorgis, F., Bonifacio, A., Sergo, V., Optimization and Characterization of Paper Made Surface Enhanced Raman Scattering (SERS) Substrates with Au and Ag NPs for Quantitative Analysis. Materials (2017) 10(12), 1365.
Mosier-Boss, P. A., Review of SERS Substrates for Chemical Sensing. Nanomaterials, 7: 6, (2017), 142.
Joshi, P., and Santhanam, V. Paper-based SERS active substrates on demand. RSC Adv., 6, 2016, 68545-68552.
Zhang, X., Dai, Z., Zhang, X., Dong, S., Wu, W., Yang, S., Xiao, X., Jiang, C. Recent progress in the fabrication of SERS substrates based on the arrays of polystyrene nanospheres Sci.China Phys. Mech. Astron. (2016) 59: 126801.
Ngo, Y.H., Li, D., Simon, G.P., and Gamier, G., Gold Nanoparticle-Paper as a Three-Dimensional Surface Enhanced Raman Scattering Substrate. Langmuir, (2012), 28: 23, 8782-8790.
Sengani, M., Grumezescu, A.M., and Rajeswari, V.D. Recent trends and methodologies in gold nanoparticle synthesis—A prospective review on drug delivery aspect. OpenNano (2017)2: 37-46.
Fan, M., Andrade, G. F., Brolo, A. G. A review on the fabrication of substrates for surface enhanced Raman spectroscopy and their applications in analytical chemistry. Anal Chim Acta.(2011) 693:7-25.
Li, X., Ballerini, D.R., and Shen, W. A perspective on paper-based microfluidics: Current status and future trends. Biomicrofluidics. (2012) 6 (1): 011301-13.
Lee, C. H., Hankus, M. E., Tian. L., Pellegrino, P. M., Singamaneni, S., Highly Sensitive Surface Enhanced Raman Scattering Substrates Based on Filter Paper Loaded with Plasmonic Nanostructures. Anal. Chem., (2011) 83: 23, 8953-8958.
Betz, J. F., Yu, W. W., Cheng, Y. White, I.M., Rubloff, G. W. Simple SERS substrates: powerful, portable, and full of potential. Phys. Chem. Chem. Phys., (2014) 16: 2224-2239.
Xiao, G., Li, Y., Shi, W., Shen, L., Chen, Q., Huang, L. Highly sensitive, reproducible and stable SERS substrate based on reduced graphene oxide/silver nanoparticles coated weighing paper. Applied Surface Science, (2017) 404:334-341.
Zhang, K., Zeng, T., Tan, X., Wu, W., Tang, Y., Zhang, H. A facile surface-enhanced Raman scattering (SERS) detection of rhodamine 6G and crystal violet using Au nanoparticle substrates. App. Surf. Sci. (2015) 347: 569-573.
Fernand, D., Lefranc, D.B., Pardanaud, C., Phan, T.N.T., Merlen, A., Hornebecq V. Detection of Rhodamine 6G at low concentrations using Raman Spectroscopy: A comparison between Ag and Au-based nanoporous substrates. European Phy. J Special Topics (2015) 224 (9) 2001-2010.
Chen, M., Zhang, Z., Liu, M., Qiu, C., Yang, H., & Chen, X. (2017). In situ fabrication of label-free optical sensing paper strips for the rapid surface-enhanced Raman scattering (SERS) detection of brassinosteroids in plant tissues. Talanta, 165, 313-320.
Wei, W., & Huang, Q. (2017). Rapid fabrication of silver nanoparticle-coated filter paper as SERS substrate for low-abundance molecules detection. Spectrochimica Acta Part A: Molecular and Biomolecular Spectroscopy, 179, 211-215.
Mu, Z., Zhao, X., Xie, Z., Zhao, Y., Zhong, Q., Bo, L., & Gu, Z. (2013). In situ synthesis of gold nanoparticles (AuNPs) in butterfly wings for surface enhanced Raman spectroscopy (SERS). Journal of Materials Chemistry B, 1(11), 1607-1613.
Wei, D., Qian, W., Wu, D., Xia, Y., & Liu, X. (2009). Synthesis, properties, and surface enhanced Raman scattering of gold and silver nanoparticles in chitosan matrix. Journal of nanoscience and nanotechnology, 9(4), 2566-2573.
Li Dan et al; "Chromatographic separation and detection of contaminants from whole milk powder using a chitosan-modified silver nanoparticles surface-enhanced Raman scattering device", Food Chemistry, vol. 224, Dec. 2016.
Huang H et al, "Synthesis of chitosan-stabilized gold nanoparticles in the absence/presence of tripolyphosphate", Biomacromolecules, American Chemical Society, vol. 5, No. Sep. 6, 2004, pp. 2340-2346.
Chevva Harish et al, Silver nanowires (AgNWs) growth in-situ on chitosan polymer matrix film for SERS application, 2017 IEEE 17th International Conference on Nanotechnology, IEEE, Jul. 2017, pp. 885-889.
Ahmed Ikram et al, "An efficient and easily retrievable dip catalyst based on silver nanoparticles/chitosan-coated cellulose filter paper", Cellulose vol. 23, No. 6 pp. 3577-3588.
Jia X et al, "Direct formation of silver nanoparticles in cuttlebone-derieved organic matrix for catalytic applications", Colloids and Surfaces A: Physiochemical and Engineering Aspects, Dec. 2008, pp. 234-240.
Written Opinion of the International Search Authority dated Apr. 15, 2019 in corresponding international application No. PCT/IN2019/050102.
International Search Report dated Apr. 15, 2019 in corresponding international application No. PCT/IN2019/050102.

* cited by examiner

RAPID, LOW-COST PROCESS FOR THE PREPARATION OF SERS SUBSTRATE AND SERS SUBSTRATE PREPARED THEREBY

CROSS REFERENCE TO RELATED APPLICATIONS

This application is a national phase of PCT application No. PCT/IN2019/050102, filed Feb. 8, 2019, which claims priority to IN patent application No. 201811023895, filed Jun. 27, 2018, all of which are incorporated herein by reference thereto.

FIELD OF INVENTION

The present invention relates to a rapid, low-cost process for the in-situ synthesis of metal nanoparticles on a substrate suitable for SERS and the resulting SERS substrate prepared thereby. In general, the present invention relates to the field of substrates for surface-enhanced Raman spectroscopy (SERS). More particularly, the present disclosure relates to a paper-based SERS substrate comprising chitosan and a metallic precursor solution prepared by in situ synthesis of gold nanoparticles using chitosan as reducing agent. The metal nanoparticles are homogenously deposited over the paper-based substrate making the paper-based substrate suitable for SERS analysis. The paper-based substrate thus developed is cost-effective, flexible, easy to load and is demonstrated to have exceptional sensitivity with detection limits of up to 1 pM. The developed SERS substrates are envisaged to have tremendous potential in the field of detection of explosives for security purposes, analysis of pharmacological samples. Trace analysis, detection of pollutants in environmental monitoring, diagnosis and point of care devices for clinical purposes.

BACKGROUND OF INVENTION AND DESCRIPTION OF PRIOR ART

Raman spectra arising from the vibrational frequencies of molecules provide 'molecular fingerprint' information that is particularly valuable in the identification and analysis of chemical/biological molecules. The inherent low sensitivity of conventional Raman scattering was overcome with the discovery of surface-enhanced Raman spectroscopy (SERS) (Smolsky et.al, Fleischmann et.al) resulting in its widespread utilization as a biomedical tool-detection/read-out system for point of care diagnosis.

In principle, SERS is a surface-sensitive technique that enhances the Raman scattering due to a sub-monolayer surface coverage on roughened coinage metal (such as gold, silver, and copper) surfaces. It exploits the electromagnetic and charge-transfer enhancement mechanism to produce a combined enhancement in the range of $10^{10}$-$10^{11}$ for optimised surfaces (Sharma et.al).

However, despite SERS being an attractive tool, it could not become a routine analytical technique due to poor SERS substrates in terms of cost-effectiveness, robustness, reproducibility and signal uniformity (Dalla Marta et.al). Nonetheless, the parallel and rapid emergence of photonics, surface sciences and nanofabrication technologies in the past two decades have accelerated development of better SERS substrates to detect a wide range of chemical and biological analytes. These metallic substrates (Ag, Cu, and Au on glass or silicon) produced using electron beam lithography, focused ion beam patterning or thermal evaporation gives precise control over the shape and size of surface features of conventional SERS substrates (Mosier-Boss et.al).

However, the above-mentioned techniques are highly sophisticated, time-consuming, costly and labor intensive. Besides, the glass and silicon-based substrates are very fragile and suffer from handling, logistics and durability constraints (Mosier-Boss et.al).

In this context, paper-based substrates (paper supports with a monolayer deposition of nanoparticles of coinage metals such as gold, silver or copper) are gaining fast popularity due to their low cost, easy availability, flexibility, robustness, and durability (Joshi and Santhaman). The natural unevenness of paper due to its cellulose-based heterogeneous fibrous web architecture offers the advantage of a pre-roughened surface with the potential to serve as excellent support for SERS substrates (Ngo et.al). The additional benefits of paper-based substrates include pre-concentration of analytes in SERS active region by lateral flow as well as quick and simple loading of samples (Joshi and Santhaman).

Deposition of nanoparticles on paper-based substrates has been exploited by various methods that include direct printing, drop-casting or dip-casting of pre-formed nanoparticle suspension, in situ chemical reduction of precursor metal salt, UV reduction of precursor metal salt or electrostatic assembly (Zhang et.al).

Development of paper-based substrates by the aforesaid methods have certain drawbacks including the loose binding of the metal with the cellulose fiber, aggregation of nanoparticles resulting in incomplete coverage, and heterogeneous depositions towards the edge of the paper due to coffee-ring effect during the drying process. Apart from these shortcomings, production of nanoparticles itself is a time-consuming process and takes several hours (at least 12-24 hours) end-to-end before the substrates are ready to use (Sengani et.al).

Reference may be made to PCT publication number WO2010073260 which discloses the preparation of paper-based SERS substrates using in situ synthesized gold/silver nanoparticles with the help of CTAB (Cetyl trimethyl ammonium bromide) and sodium citrate solution as the reducing mix. In this document, a paper comprising in situ synthesized nanoparticles is broadly claimed as a SERS substrate. It also mentions the process step of the metal precursor loaded-paper, being immersed into the boiling solution of reducing agent set to a temperature ranging from about 70 to 75 degree C. for a period of about 40 to 50 minutes. However, in the said document the paper is coated with a layer of thiophenol. Further, the metal nanoparticles are synthesized by dipping the paper in the reactant solutions, wherein the reducing agent solution comprises a combination of Sodium Citrate and Cetyl trimethyl ammonium bromide and not chitosan as in the present case. The process steps involved are numerous in nature, whereas the process of the present invention is a single step process. Further, the detection limit of the analyte in the cited document is upto millimolar or micromolar range, whereas in the present invention it is upto picomolar range.

Reference may be made to U.S. Pat. No. 9,329,177 which disclose the preparation of paper-based SERS substrates based upon the in situ synthesis of gold nanoparticles using lecithin as the reducing agent. The patent mentions the use of paper-related material as the substrate and its use to detect a surface enhanced Raman scattering signal. However, in the present invention, the reducing agent is chitosan. Further, the process steps are numerous in nature, whereas the process of the present invention is a cost-effective single step process.

Reference may be made to Chen, M. et al. 2017. Talanta. 165:313-320 which reveals the in situ synthesis of gold nanoparticle-based SERS active paper substrate using sodium borohydride as the reducing agent. The paper mentions the use of poly (y-glutamic acid) as the linker to enhance the concentration of gold nanoparticles on the paper substrate. The presence of the analyte (4-mercaptophenylboronic acid) was shown to be detectable at levels of $10^{-11}$ M. However, the cited process involves numerous steps and the reducing agent is also different, whereas the process of the present invention is a cost-effective single step process.

Reference may be made to Wei, W and Huang, Q. 2017. Spectrochimica Acta Part A: Mol and Biomol. Spectroscopy. 179:211-215 which discusses the method for the in situ synthesis of silver nanoparticles on filter paper as SERS substrate using hydrazine hydrate as the reducing agent. The paper describes the detection limit for Rhodamine B as $10^{-11}$ M. However, the cited process involves a different reducing agent and also the process of the present invention is a cost-effective single step process.

Reference may be made to Zhongde, M et al. 2013. J Mat Chem B. 11:1607-1613 which cites the method of using the wing of the butterfly as the substrate containing chitosan for the reduction of gold precursor salt as well as the SERS substrate. The reduction of the gold salt was supplemented by the addition of sodium citrate and the SERS detection limit achieved with the analyte 4-ATP (4-Aminothiophenol) was $10^{-9}$ M. However, in the present invention supplementation with sodium citrate is not required and the solid substrate used here is paper which is readily available, unlike the butterfly wing that is difficult to get. Also, the process of the present invention is rapid, cost-effective and single step process with the detection limit of the SERS substrate obtained by the claimed process is upto picomolar range.

Reference may be made to Wei, D et al. 2009. J Nanosci Nanotech. 9[4]: 2566-2573 which describes the in situ synthesis of gold/silver nanoparticles in the chitosan matrix, where chitosan served as the reducing agent, SERS substrate and as well as the stabilizer. In this paper, R6G (Rhodamine 6G) was detectable up to a concentration of $10^{-7}$ M. However, The drawbacks associated with the cited paper is that it uses chitosan film as a substrate which is fragile and needs to be attached to an expensive glass substrate for support. Apart from that, it takes around 18 hrs for the production of nanoparticles in a multistep process followed by treatment in alkaline condition with Sodium Hydroxide. Furthermore, the resulting surface with the method proposed by Wei et al. does not ensure uniform coverage of the nanoparticles. Whereas, the process used in the present invention is rapid, cost-effective and single step process with the detection limit of the SERS substrate obtained by the claimed process is upto picomolar range.

In short, it may be summarized that the in situ synthesis of gold/silver nanoparticles on cellulose paper substrate is disclosed. Further, the use of chitosan as a reducing agent in the preparation of gold and silver nanoparticles from their respective precursor salts is also described. However, the in situ synthesis of gold/silver nanoparticles on a paper substrate using chitosan as a reducing agent which is useful as a SERS substrate exhibiting sensitivity in the picomolar range has not been reported.

Thus, keeping in purview the drawbacks of the hitherto reported prior art, the inventors of the present invention realized that there exists a dire need to provide a rapid, low-cost and reproducible technique for the development of affordable SERS substrates which have ease of handling.

OBJECTIVES OF THE INVENTION

The main objective of the present invention is thus to provide a process for the preparation of inexpensive SERS substrates and SERS substrates produced thereby which obviates the drawbacks of the hitherto known prior art.

Another objective of the present invention is to provide methods for analyzing target analytes in samples using the developed SERS substrates, wherein analytes with concentration as low as 1 pM can also be detected.

Still another objective of the present invention is to provide a low-cost, efficient method to rapidly prepare metallic nanoparticles over a substrate for SERS analysis.

Yet another objective of the present invention is to provide a low-cost paper-based SERS substrate that is easy to fabricate.

Still another objective of the present invention is to provide a paper-based SERS substrate that is cost-effective, easily reproducible and flexible.

Yet another objective of the present invention is to provide a paper-based SERS substrate with homogenously deposited nanoparticles exhibiting exceptional performance, high sensitivity and long-term stability.

SUMMARY OF THE INVENTION

This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

The present invention discloses a rapid, low-cost method for in-situ synthesis of gold nanoparticles (GNPs) on a paper substrate for surface-enhanced Raman spectroscopy (SERS). The GNPs were prepared by reducing Aurocholoric acid with chitosan on a cellulose-based paper surface, in-situ. The reaction was carried out under a moisture saturated environment at various temperatures. An extremely uniform coverage of 10 nm±2 nm GNPs was obtained at 100° C. after incubation of one hour. The substrate coverage of the resulting GNPs was directly dependent on the ratio in which the precursors were added as well as the reaction time and temperature. Techniques such as TEM, SEM, and FE-SEM were utilized to determine the shape, size and distribution of the GNPs on a paper substrate. The gold nanoparticle bound paper-based SERS substrate showed exceptional performance and long-term stability. The detection limit as low as 1 pM as a function of R6G concentrations was achieved. The developed paper-based SERS substrates are cost-effective, reproducible and provide high sensitivity.

In an embodiment, the present invention provides methods for manufacturing SERS substrates. The method begins with providing a substrate with a top surface and a bottom surface. This is followed by applying reactants comprising a chitosan solution and a metallic precursor solution on the top surface. Then the substrate is incubated under humidifying conditions at a higher temperature for a predetermined duration. Such an incubation results in the rapid, direct in-situ reduction of the metallic precursor solution by the chitosan solution thereby producing metal nanoparticles. The metal nanoparticles are homogenously deposited over the substrate making the substrate suitable for SERS analysis. In preferred embodiments, the substrates are paper-based SERS substrates deposited with gold nanoparticles.

In another embodiment, the present invention provides SERS substrates comprising a top surface and a bottom surface. The top surface is homogenously deposited with a plurality of metal nanoparticles. The metal nanoparticles are formed by direct in-situ reduction of a metallic precursor solution by a chitosan solution. Both the solutions are applied directly onto the top surface and incubated under humidifying conditions at a higher temperature for a predetermined duration.

In yet another embodiment, the present invention provides methods of detecting target analytes in samples. The method begins with the step of providing a SERS substrate as described in the above paragraphs. This is followed by the application of the serially diluted sample solution with the target analyte onto the top surface of the substrate. This is followed by detecting the target analyte based on the Raman spectra.

BRIEF DESCRIPTION OF THE ACCOMPANYING DRAWINGS

Various embodiments of the present invention are illustrated more clearly in the drawings accompanying the specification.

DETAILED DESCRIPTION OF THE INVENTION

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item.

According to a non-limiting exemplary embodiment of the present disclosure, methods for manufacturing SERS substrates and SERS substrates thereof are disclosed. The present invention further discloses methods for analysing target analytes in samples using the same.

The term "paper" used herein refers to a porous material obtained from fibres of cellulosic or cellulosic derivatives. The material is processed from wood, cotton or any other natural or synthetic sources.

The term "higher temperature" disclosed herein refers to temperatures ranging from about 40° C. to 120° C.

Exemplary embodiments of the present disclosure are directed towards methods for manufacture of SERS substrates. The method begins with providing a substrate with a top surface and a bottom surface. This is followed by applying reactants comprising a chitosan solution and a metallic precursor solution on the top surface. In different embodiments, the concentration of the chitosan solution ranges from about 0.5% to 2% in acetic acid aqueous solution ranging from 0.5% to 5% and in preferred embodiments, 1% chitosan solution in 1% acetic acid is used for the preparation of nanoparticles. Though low molecular weight chitosan is preferred, medium as well as high molecular weight chitosan can also be used for the synthesis of metal nanoparticles without limiting the scope of the present disclosure.

In different embodiments, the concentration of the metallic precursor solution ranges from about 0.75 mM to about 10 mM and in preferred embodiments, the concentration is about 3.75 mM. The reactants can be applied onto the top surface either after mixing them together or separately one after another mixing them therein without limiting the scope of the present disclosure.

In some embodiments, the metallic precursor solution is first added to the top surface followed by chitosan. Then the substrate is incubated under humidifying conditions at a higher temperature for a predetermined duration. Preferably the incubation is carried out under saturated humidifying conditions. Such an incubation results in the rapid, direct in-situ reduction of the metallic precursor solution by the chitosan solution thereby producing metal nanoparticles. The metal nanoparticles are homogenously deposited over the substrate making the substrate suitable for SERS analysis. In preferred embodiments, the substrates are paper-based SERS substrates deposited with gold nanoparticles.

Other exemplary embodiments of the present subject matter are directed towards SERS substrates.

The SERS substrates are paper-based, glass (oxide)-based or silicon-based substrates (Fan et.al) (Betz et. al) through any other suitable SERS substrates that are known in the art can be used without limiting the scope of the present disclosure. The SERS substrates comprise of a top surface and a bottom surface. The top surface is homogenously deposited with a plurality of metal nanoparticles. The metal nanoparticles are gold, silver, copper nanoparticles or any other metallic nanoparticles that are known in the art without limiting the scope of the present disclosure. The metal nanoparticles are formed by direct in-situ reduction of a metallic precursor solution by a chitosan solution. Both the solutions are applied directly onto the paper surface and incubated under humidifying conditions at a higher temperature for a predetermined duration. In preferred embodiments, the substrates are paper-based SERS substrates deposited with gold nanoparticles.

Other exemplary embodiments of the present subject matter are directed towards methods of detecting target analytes in samples. The method begins with the step of providing a SERS substrate as described in above paras. This is followed by the application of the serially diluted sample solution having the target analyte onto the substrate. This is followed by the detection of the Raman spectra of the sample substrates loaded on the substrate. The spectra generated are then interpreted to detect the target analyte.

EXAMPLES

The following examples are given by way of illustration only and therefore should not be construed to limit the scope of the present invention in any manner.

Example 1

Substrate Preparation

Figure 1:
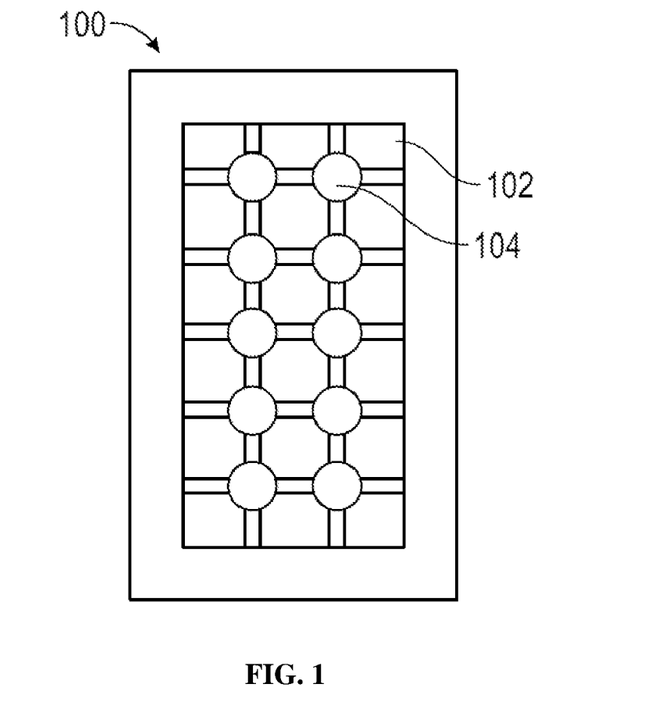
FIG. 1 represents a top surface of the paper-based substrate with a hydrophilic-hydrophobic contrast, in accordance with a non-limiting exemplary embodiment of the present disclosure.

FIG. 1 depicts a paper-based substrate 100 made of Whatman qualitative filter paper of Grade 4 (thickness 0.205 mm, GE-Wipro, India), designed using CorelDraw® Suite X8 software package and cut out using a computer-controlled laser cutting and engraving machine (Model CMA 6040, GD Han's Yueming Laser Group Co. Ltd., China). The paper-based substrate is patterned with hydrophobic zones to create a hydrophobic-hydrophilic contrast. The patterning of the hydrophobic zone can be done by any technique known in the art and by using any hydrophobic agent known in the art without limiting the scope of the present disclosure. The hydrophobicity can be created by physical blocking of pores on the paper-based substrate by using agents such as Photoresist and poly dimethyl siloxane, by depositing agents such as polystyrene or wax on the substrate or by chemical modification of the paper surface by agents such as alkyl ketene dimer (Li et al., 2012). Thus obtained paper devices with a hydrophilic-hydrophobic contrast have a top surface 102 comprising multiple hydrophilic reactive discs 104 (5 mm) that serve as the active area. The paper devices are laminated completely with plastic film on a bottom surface. In this embodiment, the device has 10 such reactive discs that can be used independently as single SERS substrate. The reactive disc is held apart from each other by four paper supports or fragments that were made hydrophobic using permanent ink. These hydrophobic supports act as barriers to confine the reaction on the disc itself as well as to avoid reactant intermixing from adjacent discs. These support arms also provide sturdiness and help in eliminating the deformation of the devices that could occur due to wetting of the paper.

Example 2

Preparation of Gold Nanoparticles Using Chitosan on Paper Discs

Figure 2:
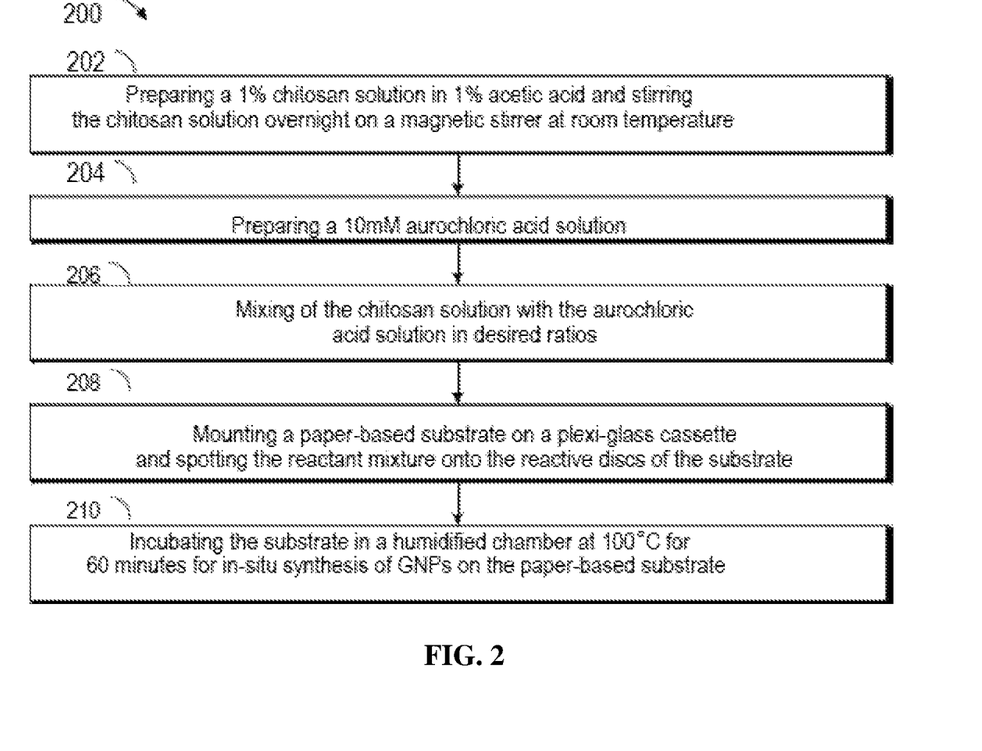
FIG. 2 represents a flowchart depicting the in-situ synthesis of gold nanoparticles (GNP) on the paper-based substrate, in accordance with a non-limiting exemplary embodiment of the present disclosure.

FIG. 2 depicts a step by step procedure 200 for the in-situ synthesis of gold nanoparticles (GNP) on the paper-based substrate. All glassware used in the present study were cleaned in freshly prepared chromic acid solution followed by thorough washing with MilliQ water prior to use. The procedure begins with step 202 for preparing a 1% chitosan (low molecular weight) solution in 1% acetic acid and stirring the chitosan solution overnight on a magnetic stirrer at room temperature as the solubility of the chitosan is low. A stock solution of 1 M aurochloric acid ($HAuCl_4$) was prepared in Milli-Q water which was further diluted to a 10 mM concentration working solution, as given in step 204. At step 206, the chitosan solution is mixed with the aurochloric acid solution in desired ratios (such as chitosan:aurochloric acid: 25:3, 25:6, 25:9, 25:12 and 25:15) and the final volume was made upto 40 µl using MilliQ water for each reaction. This was followed by mounting the paper-based substrate on a plexiglass cassette and directly spotting the resultant reactant mixture onto the 5 mm reactive discs of the substrate at step 108. Finally, at step 210, the substrate is incubated in a humidified chamber under saturated humidifying conditions at 100 degrees C. for 60 minutes for in-situ synthesis of GNPs on the paper-based substrate.

Example 3

Characterization of As-Synthesized Gold Nanoparticles on a Paper Substrate:

UV/Vis spectroscopy analysis: The UV-Vis absorption spectra between 200 to 800 nm were collected using a SHIMADZU (UV-2600) UV-VIS spectrophotometer. For analysis, the nanoparticle-containing solution was directly harvested from the paper-based devices as soon as the incubation time at a particular temperature was over. The purpose of UV-VIS spectrophotometric study was to evaluate the size of the gold nanoparticles at different time frames (15, 30, 45 & 60 minutes) for a fixed ratio of reducing agent to precursor salt when incubated in a hot air oven at 100 degrees C.

Figure 3A:
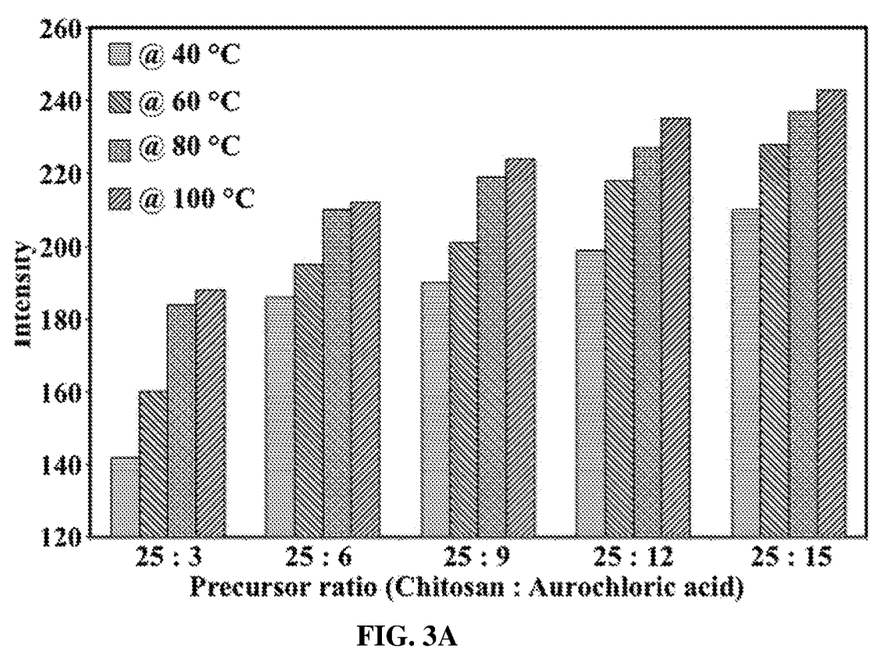
FIGS. 3A and 3B are graphical representations of the colour intensity of paper-based devices with gold nanoparticles; (3A) Effect of various reduction temperatures with fixed reduction time (60 mins) (3B) Effect of various reduction time with fixed reduction temperature (100 degrees C.).

FIG. 3A demonstrates the effect of various temperatures (25, 40, 60, 80 and 100 degrees C.) at a fixed reaction time of 1 hr. To evaluate the size of nanoparticles produced on the paper substrate, the colour intensity of semi-dried SERS active area was analysed using ImageJ software. It could be clearly seen from the plot that the colour intensity increased with the elevation in temperature due to an increase in in-situ reduction of the Aurochloric acid to GNP's. Thus indicating that gold nanoparticle production on paper is directly proportional to the increase in reduction temperature.

Figure 3B:
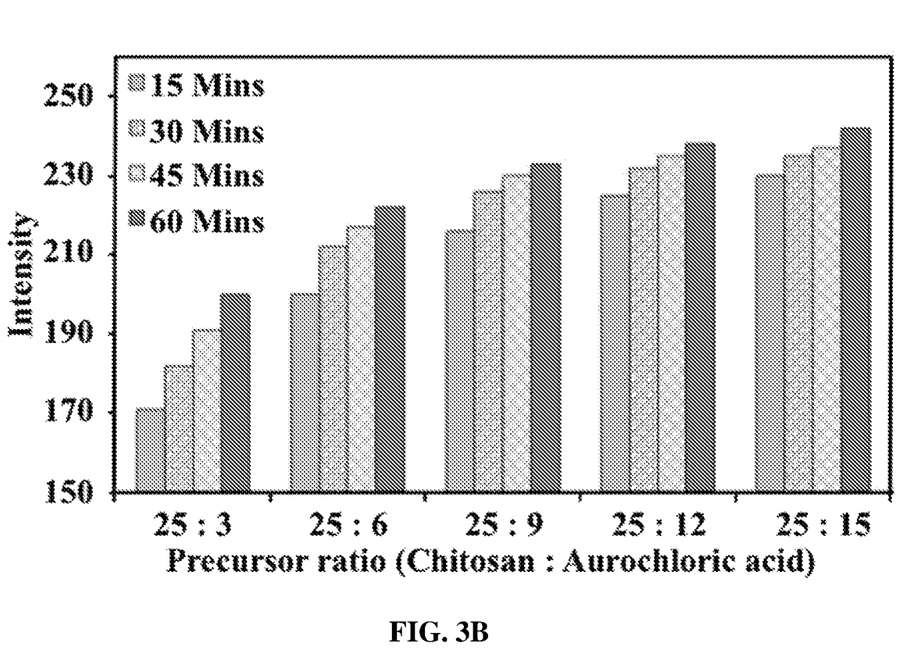

FIG. 3B depicts the results of the efforts made to study the effect of varying precursor ratio of aurochloric acid and chitosan on GNP production and the analysis of the color intensity of semi-dried SERS active area. The experiment was carried out at 5 different ratios along with varying reduction time of 15, 30, 45 and 60 mins. FIG. 3B shows the colour intensity plotted against the different ratio of precursors at various reduction time. From the plot it can be inferred that as the reduction time and/or the amount of aurochloric acid component is increased, the production of nanoparticles also increases, as evident by change in the colour of the paper devices from white (left side of the plot) to dark red (right side of the plot). Although a plateau seems to be approaching in the plot, which means that further production of GNP's would not be possible by increasing the reduction time and/or the amount of Aurochloric acid component. This could be due to the reduction limit of chitosan towards Aurochloric acid in the given time, temperature and amount. Although it was not tested, in order to get a higher deposition and coverage of GNP's on paper, either the amount of precursor solution could be increased from 40 µL to higher volumes by maintaining the precursor mixture ratio or multiple depositions on the same substrate could be employed.

SEM analysis: Scanning Electron Microscopy characterization was performed using 3400N Hitachi, Japan to understand the size, morphology, and distribution of the as-synthesized gold nanoparticles, SEM. The system was operated at 5 kV directly on the gold deposited paper substrate without any conductive film coating. A lower accelerating voltage of 5 kV was specifically applied to avoid the charring of the paper surface.

Figure 4:
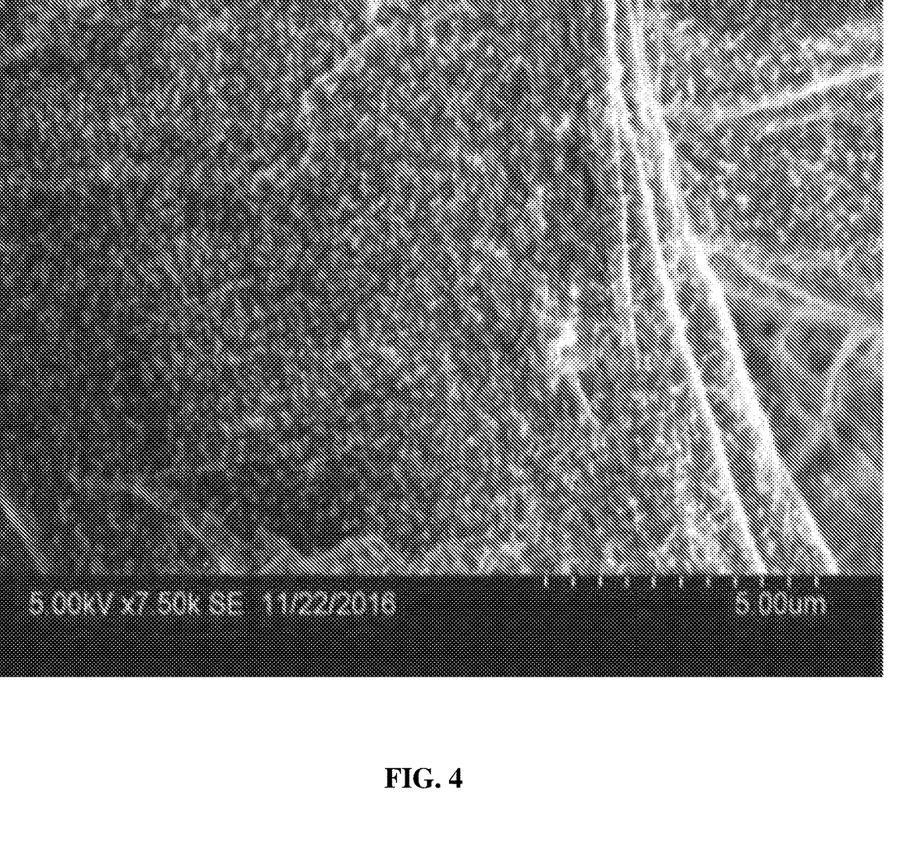
FIG. 4 represents an SEM image showing the as-synthesized GNP bound on paper-based devices at 100 degrees C. reduction temperature and a reduction time of 60 minutes with precursor mix of 25:15:chitosan:aurochloric acid.

FIG. 4 depicts the low magnification SEM images of the paper devices with the as-synthesised gold nanoparticles which show a uniform, densely packed and well-arranged gold nanoparticles on the paper device fibres. Such kind of assembly is well suited for obtaining high signal enhancement for SERS.

The EDX analysis report illustrated distinct elemental gold peaks. Due to the presence of GNP's of ~10 to 12 nm size, a significant elemental gold peak was observed during EDX analysis. The paper devices used in the present study are mainly composed of cellulose, which by nature is rich with a hydroxyl group. This hydroxyl group has an affinity towards positively charged species. The GNP's produced in the present case is reduced by chitosan and hence are capped with positively charged chitosan. The GNP's attached to the paper devices, withstood intensive washing steps with both water and ethanol without any notable changes in its density or arrangement, thus proving their stability and suitability as paper-based SERS substrate.

FE-SEM analysis: To get a high-resolution image of the gold deposited paper substrate, FE-SEM analysis was done. The gold deposited paper substrates were first coated with a 2 nm thick platinum film and then loaded into Jeol JSM-7610F FEG SEM instrument. The platinum film was coated to provide a conductive film such that the charring of the paper surface could be avoided. A low accelerating voltage (EHT) of 5 kV with multiple working distances ranging between 7.9 mm to 10.3 mm was applied to capture images with magnification varying from 5000× to 50,000×. Selected FE-SEM images were also scrutinized with Energy Dispersive X-Ray Spectroscopy (EDS/EDX) to obtain the chemical composition at an EHT voltage of 5 kV and a working distance of approximately 9.6 mm. The high magnification FE-SEM images revealed that the micro and the nanofibers of the paper surface are covered with the gold nanoparticles uniformly.

TEM analysis: TEM analysis was also done to estimate the size of the as-synthesized gold nanoparticles. For sample preparation, 200 mesh Copper grids (Carbon coated) were glow discharged for 30 sec using Polaron carbon evaporator, followed by loading of 5 µl of samples on the glow discharged grids and allowed to dry for 10 mins. Excess sample was wicked off using Whatman filter paper and allowed to dry for another 30 mins. The dried samples thus obtained were loaded in the TEM (JEOL JEM-2100) on a single tilt holder and the images were captured and analysed at 120 kV.

Figure 5:
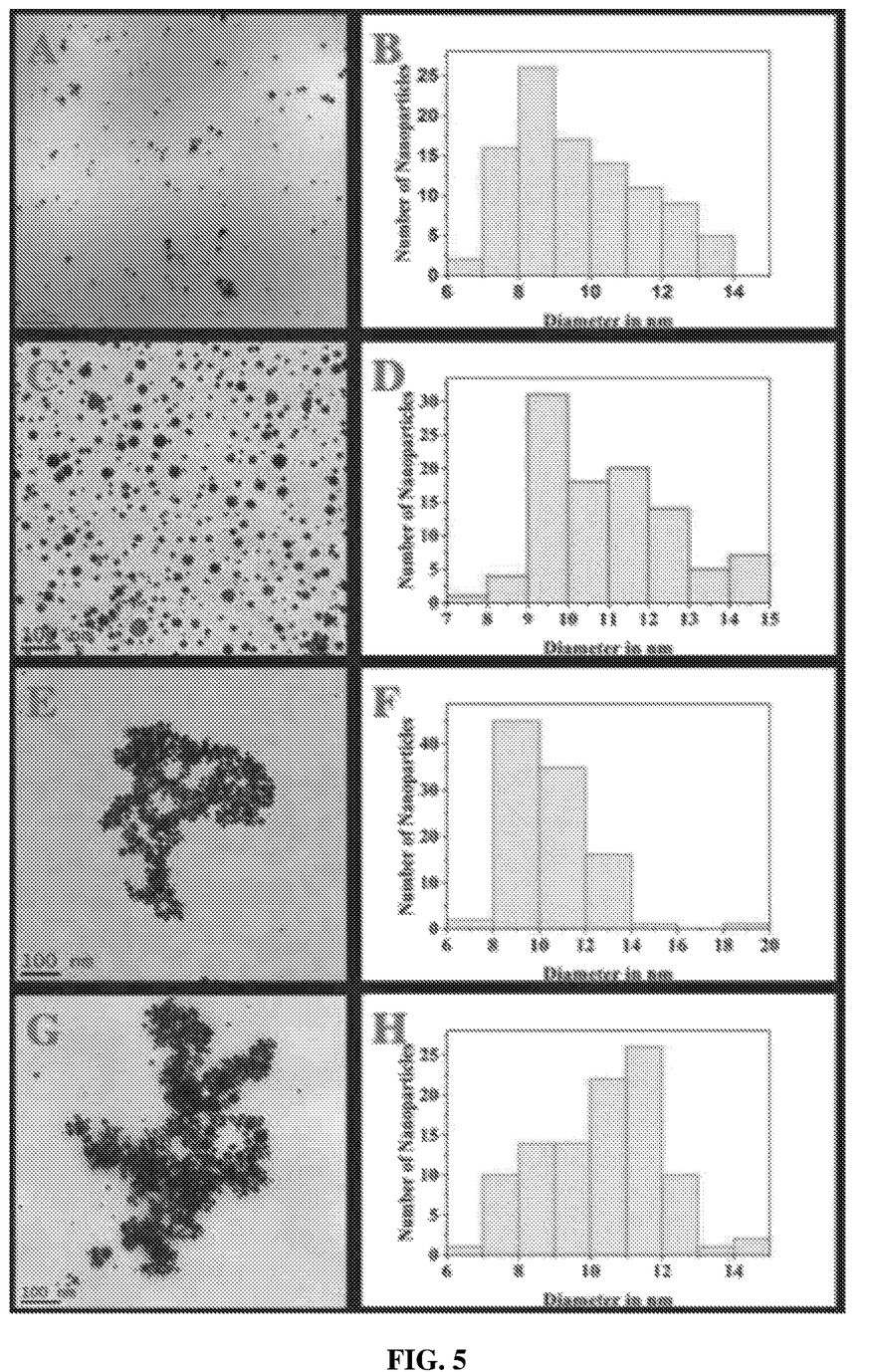
FIG. 5 represents the transmission electron microscopy images and histograms of particle size distribution at 100 degrees C. with various reduction time and fixed precursor mix ratio of 25:15:chitosan:aurochloric acid; (A & B) 15 mins, (C & D) 30 mins, (E & F) 45 mins and (G & H) 60 mins.

FIG. 5 demonstrates the TEM images analysed by Image J software and the average size distribution of around 100 particles plotted into a histogram. TEM images clearly demonstrate that the concentration of the GNP's increased monotonically with the increase in reduction time of the precursors, as the particles distribution was much denser at a higher reduction time of 60 mins.

Example 4

Raman Spectra of R6G on Paper-Based SERS Substrates

To evaluate the SERS performance of the as-synthesized paper-based substrate, Rhodamine 6G [R6G] was used as a Raman marker. Control paper (for normal Raman scattering) and as-synthesized GNP coated paper (for surface-enhanced Raman scattering) substrates were both loaded with 2.5 µL of Rhodamine 6G at 10 µM concentration and air-dried overnight. The sample substrates thus prepared were analysed via Renishaw In Via Raman microscope (Renishaw InVia, UK) with 633 nm edge excitation laser with 10% laser power. An integration time of 1 sec and an exposure time of 1 sec was used for each sample with 10 accumulations using a 20× objective. Several scans were obtained at different spots on the paper-based SERS substrates. Post-processing of the collected scans was done using wire 3.4 software supplied with the instrument. Before collecting the SERS spectra, laser alignment and the sample position was calibrated using standard silica reference at 520 cm$^{-1}$.

Figure 6:
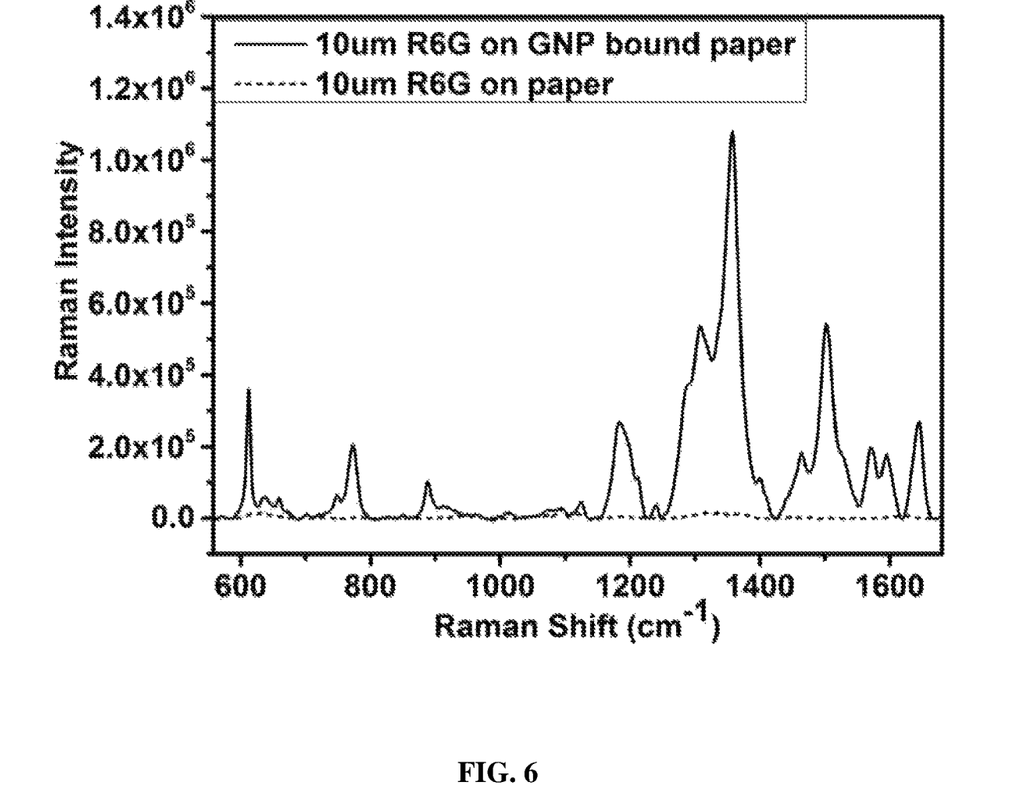
FIG. 6 represents the surface enhanced Raman spectra (SERS) of 2.5 µL of 10 µM Rhodamine 6G adsorbed on a paper substrate with and without the as-synthesized GNP's using a laser excitation wavelength of 633 nm.

FIG. 6 depicts the typical SERS spectra for 2.5 µL of 10 µM R6G on a paper substrate with and without gold nanoparticles (Zhang et. al) (Fernand et. al). The spectra achieved specifically matches (with an error of ±3) with the spectroscopic signatures of R6G with high signal to noise ratio and characteristic vibrational band at 606 cm$^{-1}$ (for C-C-C ring in-plane bend vibration), 776 cm$^{-1}$ (for C-H out-of-plane bend vibration), 1127, 1185 cm$^{-1}$ (for C-H in-plane bend vibration) and at 1312, 1361, 1506, 1574, 1648 cm$^{-1}$ (for aromatic C-C stretching vibration) (Xiao et. al). When compared with the control paper substrate showing the normal Raman spectrum of R6G, many fold enhancements was observed on GNP coated substrate.

For understanding the effect of heterogeneity of paper surface and its imaging, SERS Streamline™ scans were also made using 633 nm streamline laser at 100% laser power (Lee et.al). An integration time of 10 sec and 2 sec exposure time was used for each sample using a 20× objective. An area of 1100 µm×1300 µm was scanned and the data obtained were processed with wire 3.4 software.

The Raman mapping (Streamline™ mapping images) of the as-synthesized paper-based substrate adsorbed with 2.5 µL of 1 µM Rhodamine 6G was done. The Raman intensity map using a laser excitation wavelength of 633 nm was plotted. The optical micrograph of the region where Raman mapping was performed was also done. Comparison of the above two images indicated a uniform distribution of particles and hence homogenous Raman intensity; the red coloured area is where the laser is focused. On the other hand, the black coloured area indicates a region that is out-of-focus. Some variation in intensity was observed along the same cellulose fibres, which could be attributed to the unevenness caused due to the adsorption of the gold nanoparticles on the fibres (Lee et.al).

Furthermore, SERS performances for Rhodamine 6G at various concentrations ranging between 1 µM to 10 µM were also tested, for which a volume of 2.5 µL of R6G was added onto the paper substrate deposited with GNP's and air-dried overnight in dark before SERS measurement. SERS spectra were collected with 633 nm edge excitation laser at 50% laser power. An integration time of 1 sec and 1 sec exposure time was used with 10 accumulations using a 20× objective. Multiple scans were obtained from different locations within the substrate and the final SERS intensity calculation was done by averaging three replicates. Post-processing of the collected scans was again done using Wire 3.4 software.

Figure 7A:
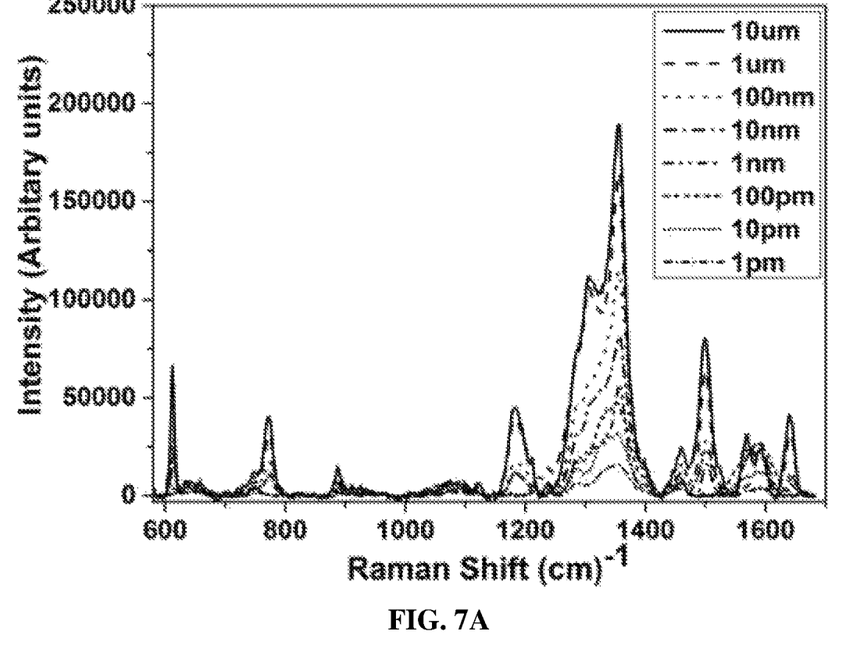
FIG. 7A represents the SERS spectra of different concentrations of Rhodamine 6G adsorbed on the as-synthesized GNP bound paper-based substrate.

FIG. 7A depicts that even with concentrations as low as 1 pM, the characteristic bands of R6G were clearly perceived. The SERS spectra gradually improved with the increase in concentration from 1 pM to 1 µM thereby showing the direct dependence of intensity with the amount of the Raman probe molecule.

Figure 7B:
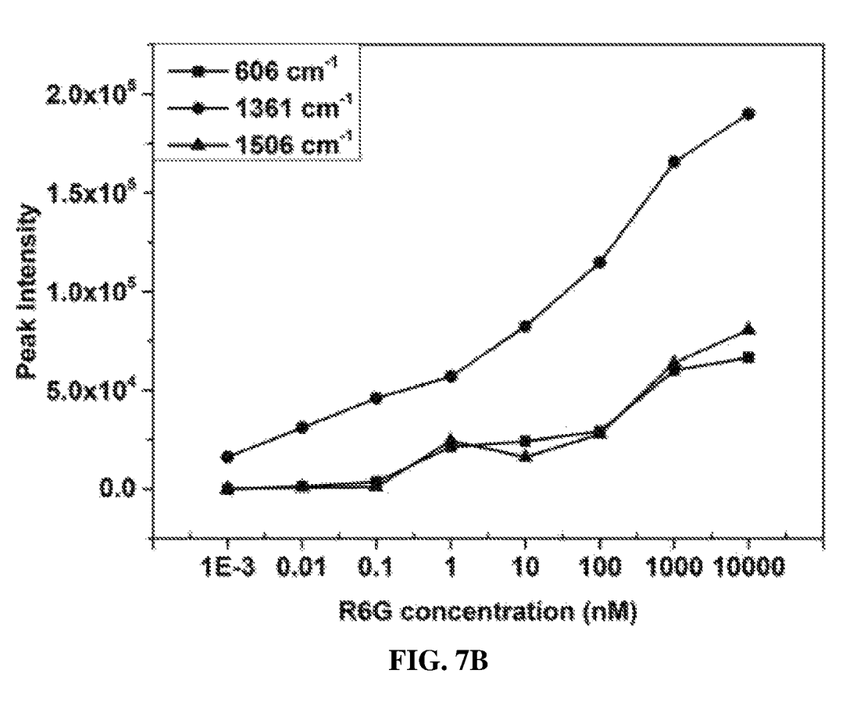
FIG. 7B shows the SERS intensity of the main peaks at different peak intensities with respect to the different concentration of Rhodamine 6G.

FIG. 7B depicts the intensities of R6G signature bands at 606, 1361 and 1506 cm$^{-1}$ when plotted against their different concentrations respectively and showing a linear regression.

Furthermore, the stability of the substrates was also tested by doing multiple measurements on the same substrate using the same setting over a period of few months and the spectra achieved was almost identical with an average shift of ±6 for the specific R6G signature bands between different scans.

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub-combinations of the various features described herein above as well as variations and modifications thereof, which would occur to persons skilled in the art upon reading the foregoing description.

Advantages of the Invention

The present method uses paper as the solid support matrix which is affordable and easily available.

The present method is rapid and provides high-quality SERS substrate in 60 mins with high reproducibility.

The paper-based SERS substrate demonstrated in the present invention shows a higher sensitivity in pico-molar range for R6G analyte.

The present method provides a robust and flexible SERS substrate that is easy to handle and store.

The present methods for the preparation of SERS substrate ensure uniform coverage of nanoparticles on the surface.

REFERENCES

1. Smolsky J, Kaur S, Hayashi C, Batra S K, Krasnoslobodtsev A V. Surface-Enhanced Raman Scattering-Based Immunoassay Technologies for Detection of Disease Biomarkers. Frosch T, ed. Biosensors. 2017; 7 (1):7.
2. Fleischmann, M., Hendra, P. J. and McQuillan, A. J., Raman spectra of pyridine adsorbed at a silver electrode. Chem. Phys. Lett., 1974, 26, 163-166.
3. Sharma, B., Frontiera, R. R., Henry, A. I., Ringe, E., Van Duyne, R. P., SERS: materials, applications, and the future, Mater. today 15(1), 2012, 16-25.
4. Dalla Marta, S., Novara, C., Giorgis, F., Bonifacio, A., Sergo, V., Optimization and Characterization of Paper Made Surface Enhanced Raman Scattering (SERS) Substrates with Au and Ag NPs for Quantitative Analysis. Materials (2017) 10(12), 1365.
5. Mosier-Boss, P. A., Review of SERS Substrates for Chemical Sensing. Nanomaterials, 7: 6, (2017), 142.
6. Joshi, P., and Santhanam, V. Paper-based SERS active substrates on demand. RSC Adv., 6, 2016, 68545-68552.
7. Zhang, X., Dai, Z., Zhang, X., Dong, S., Wu, W., Yang, S., Xiao, X., Jiang, C. Recent progress in the fabrication of SERS substrates based on the arrays of polystyrene nanospheres Sci. China Phys. Mech. Astron. (2016) 59: 126801.
8. Ngo, Y. H., Li, D., Simon, G. P., and Garnier, G., Gold Nanoparticle-Paper as a Three-Dimensional Surface Enhanced Raman Scattering Substrate. Langmuir, (2012), 28: 23, 8782-8790.
9. Sengani, M., Grumezescu, A. M., and Rajeswari, V. D. Recent trends and methodologies in gold nanoparticle synthesis—A prospective review on drug delivery aspect. OpenNano (2017)2: 37-46.
10. Fan, M., Andrade, G. F., Brolo, A. G. A review on the fabrication of substrates for surface enhanced Raman spectroscopy and their applications in analytical chemistry. Anal Chim Acta. (2011) 693:7-25.
11. Li, X., Ballerini, D. R., and Shen, W. A perspective on paper-based microfluidics: Current status and future trends. Biomicrofluidics. (2012) 6 (1): 011301-13.
12. Lee, C. H., Hankus, M. E., Tian. L., Pellegrino, P. M., Singamaneni, S., Highly Sensitive Surface Enhanced Raman Scattering Substrates Based on Filter Paper Loaded with Plasmonic Nanostructures. Anal. Chem., (2011) 83: 23, 8953-8958.
13. Betz, J. F., Yu, W. W., Cheng, Y. White, I. M., Rubloff, G. W. Simple SERS substrates: powerful, portable, and full of potential. Phys. Chem. Chem. Phys., (2014) 16: 2224-2239.
14. Xiao, G., Li, Y., Shi, W., Shen, L., Chen, Q., Huang, L. Highly sensitive, reproducible and stable SERS substrate based on reduced graphene oxide/silver nanoparticles coated weighing paper. Applied Surface Science, (2017) 404:334-341.
15. Zhang, K., Zeng, T., Tan, X., Wu, W., Tang, Y., Zhang, H. A facile surface-enhanced Raman scattering (SERS) detection of rhodamine 6G and crystal violet using Au nanoparticle substrates. App. Surf. Sci. (2015) 347: 569-573.
16. Fernand, D., Lefranc, D. B., Pardanaud, C., Phan, T. N. T., Merlen, A., Hornebecq V. Detection of Rhodamine 6G at low concentrations using Raman Spectroscopy: A comparison between Ag and Au-based nanoporous substrates. European Phy. J Special Topics (2015) 224 (9) 2001-2010.

The invention claimed is:

1. A process for preparing a SERS substrate comprising:
   [a] providing a paper-based substrate having a top surface and a bottom surface;
   [b] applying reactants comprising a chitosan solution and a metallic precursor solution on the top surface of the substrate of step [a]; and
   [c] incubating the substrate of step [b] under saturated humidity at a temperature in the range of 40 to 120° C. for a period in the range of 15 to 60 mins, whereby said incubation results in direct in situ reduction of the metallic precursor by the chitosan to produce metal nanoparticles deposited on the top surface of the substrate,
   wherein the top surface of the paper-based substrate comprises a hydrophilic zone and one or more hydrophobic zones surrounding the hydrophilic zone.

2. The process as claimed in claim 1, wherein the paper-based substrate is derived from cellulose or cellulosic derivatives.

3. The process as claimed in claim 1, wherein the chitosan solution comprises from 0.5 to 2.0% of chitosan in a 0.5 to 5% acetic acid aqueous solution.

4. The process as claimed in claim 1, wherein the concentration of the metallic precursor solution ranges from 0.75 mM to 10 mM.

5. The process as claimed in claim 1, wherein the produced metal nanoparticles are selected from gold nanoparticles and silver nanoparticles.

6. The process as claimed in claim 1, wherein the metallic precursor solution is selected from aurochloric acid and silver nitrate.

7. The process as claimed as claim 1, wherein the substrate is incubated at a temperature of 100° C. for 1 hour.

8. A SERS substrate made by a process according to claim 1.

9. The process as claimed in claim 1, wherein the concentration of the metallic precursor solution is 3.75 mM.

10. The process as claimed in claim 1, wherein the paper-based substrate is derived from a natural source.

11. A process for preparing a SERS substrate comprising:
[a] providing a paper-based substrate having a top surface and a bottom surface;
[b] applying reactants comprising a chitosan solution and a metallic precursor solution on the top surface of the substrate of step [a]; and
[c] incubating the substrate of step [b] under saturated humidity at a temperature in the range of 40 to 120° C. for a period in the range of 15 to 60 mins, whereby said incubation results in direct in situ reduction of the metallic precursor by the chitosan to produce metal nanoparticles deposited on the top surface of the substrate,
wherein the process further comprises, prior to step [a], mounting the paper-based substrate on a plexiglass cassette such that the top surface of the paper-based substrate is facing away from the plexiglass cassette.

12. A process for preparing a SERS substrate comprising:
[a] providing a paper-based substrate having a top surface and a bottom surface;
[b] applying reactants comprising a chitosan solution and a metallic precursor solution on the top surface of the substrate of step [a]; and
[c] incubating the substrate of step [b] under saturated humidity at a temperature in the range of 40 to 120° C. for a period in the range of 15 to 60 mins, whereby said incubation results in direct in situ reduction of the metallic precursor by the chitosan to produce metal nanoparticles deposited on the top surface of the substrate,
wherein the top surface of the paper-based substrate comprises a plurality of hydrophilic zones and a plurality of hydrophobic zones, where each of the plurality of hydrophilic zones are separated from each other by one or more of the plurality of hydrophobic zones.

13. The process as claimed in claim 12, wherein the paper-based substrate is derived from cellulose or cellulosic derivatives.

14. The process as claimed in claim 12, wherein the produced metal nanoparticles are selected from gold nanoparticles and silver nanoparticles.

15. A SERS substrate made by a process according to claim 12.

16. The process as claimed in claim 11, wherein
the paper-based substrate is derived from cellulose or cellulosic derivatives, and
the produced metal nanoparticles are selected from gold nanoparticles and silver nanoparticles.

17. A SERS substrate made by a process according to claim 11.

* * * * *